United States Patent
Gazzara

(12) 
(10) Patent No.: US 6,481,845 B1
(45) Date of Patent: Nov. 19, 2002

(54) EYEWEAR WITH DETACHABLE LENS PORTION

(76) Inventor: Peter J. Gazzara, 8 Woodbine St., Reading, MA (US) 01867

( * ) Notice: Subject to any disclaimer, the term of this patent is extended or adjusted under 35 U.S.C. 154(b) by 0 days.

(21) Appl. No.: 09/925,784

(22) Filed: Aug. 9, 2001

(51) Int. Cl.[7] .............................................. G02C 11/08
(52) U.S. Cl. ............................ 351/62; 351/158; 2/436; 2/452
(58) Field of Search ............................. 351/41, 44, 62, 351/154, 155, 158; 2/12, 13, 15, 435–438, 441, 452

(56) References Cited

U.S. PATENT DOCUMENTS

| | | |
|---|---|---|
| 3,233,249 A | 2/1966 | Baratelli |
| 4,701,965 A | 10/1987 | Landis |
| 4,824,233 A | 4/1989 | Jannard |
| 4,951,322 A | 8/1990 | Lin |
| 5,042,094 A | 8/1991 | Sadowsky |
| 5,088,114 A | 2/1992 | Salace et al. |
| 5,245,709 A | 9/1993 | Shipcott |
| 5,319,396 A | 6/1994 | Cesarczyk |
| 5,339,119 A | 8/1994 | Gardner |
| 5,379,463 A | 1/1995 | Schleger et al. |
| 5,379,464 A | 1/1995 | Schleger et al. |
| 5,410,763 A | 5/1995 | Bolle |
| 5,423,092 A | 6/1995 | Kawai |
| 5,495,303 A | 2/1996 | Kolentsi |
| 5,528,320 A | 6/1996 | Specht et al. |
| 5,584,078 A | 12/1996 | Saboory |
| 5,617,588 A | 4/1997 | Canavan et al. |
| 5,765,223 A | 6/1998 | McCausland |
| 5,768,716 A | 6/1998 | Porsche |
| 5,841,505 A | 11/1998 | Bolle |
| 5,970,514 A | 10/1999 | Wang-Lee |
| 6,116,731 A | 9/2000 | Fuchs |
| 6,227,664 B1 * | 5/2001 | Pavlak .......................... 351/62 |

* cited by examiner

*Primary Examiner*—Huy Mai
(74) *Attorney, Agent, or Firm*—O'Connell Law Firm

(57) ABSTRACT

An element of eyewear with a detachable lens portion comprising a first eyewear portion comprising a lens portion, a second eyewear portion comprising a frame portion, at least one projection that extends from the lens portion, and at least one aperture in the frame portion whereby the lens portion can be removably and replacably coupled with the frame portion. The at least one projection can be formed of resiliently compressible material. A plurality of projections can extend from the first eyewear portion, and a plurality of aligned apertures can be provided in a bridge segment of the frame portion. The projections can be longer than the bridge segment is thick such that distal ends of the projections will contact the forehead of the wearer to space the bridge segment therefrom. The element of eyewear can be an eye shield with a panel of translucent material comprising the lens portion.

30 Claims, 5 Drawing Sheets

EYEWEAR WITH DETACHABLE LENS PORTION

FIELD OF THE INVENTION

The invention disclosed herein relates generally to eyewear. Stated more particularly, the present patent discloses and protects an element of eyewear with a readily removable and replaceable lens portion.

BACKGROUND OF THE INVENTION

In 1987, the Center for Disease Control and Prevention (the CDC) published "Recommendations for Prevention of HIV Transmission in Health-Care Settings" where the CDC recommended that blood and body fluid precautions be used for all patients regardless of their known bloodborne infection status. Under these recommended precautions, blood and certain body fluids of all patients are considered potentially infectious for human immunodeficiency virus (HIV), hepatitis B virus (HBV), and other bloodborne pathogens. As such, the CDC's precautions are commonly referred to as Universal Precautions in that they are practiced at all times for all patients and in all situations in which exposure to blood or potentially infectious materials may occur. Universal Precautions were mandated into standards in 1991 by the Occupational Safety and Health Administration (OSHA).

Among the required precautions is that medical personnel and laboratory workers must wear eye shields to prevent blood and other bodily fluids from reaching their eyes through splattering, splashing, or aerosolization. To be completely effective, an eye shield must protect the wearers eyes and, if desired, nose and mouth. The eye shield should do so without regard to the direction in which the wearer faces.

Similar needs for eye and face protection exist in other fields of endeavor. For example, when painting or applying other liquid coatings to a surface by rolling, brushing, spraying or the like, material can spatter and drip onto the person's eyes and face. Such spattering and dripping can be particularly problematic where the surface to be coated is above the person applying the material. For a number of reasons including safety, comfort, and convenience during cleanup, practitioners commonly seek to prevent such spattering and dripping.

As one would expect in light of the foregoing, the prior art discloses a wide variety of eye and face shields. However, even when combined, the eye and face shields of the prior art have left room for significant improvements in structure, function, convenience, and comfort. For example, many eye shields make it difficult or uncomfortable for the wearer to wear eyeglasses simultaneously with the shield. Furthermore, many shields fail to provide absolute protection to the wearer from droplets or the like that might go over or around a panel-type shield. This is particularly true of many shields that attempt to accommodate the wearing of eyeglasses since they must be spaced from the wearer's face and forehead. On a similar note, one will be aware that most if not all shields do not allow the wearer to adjust the distance of the lens or shield portion from the wearer's face. With this, such shields cannot readily accommodate wearer's with different needs, preferences, or bodily configurations.

Even further, one knowledgeable in the art will be aware that most eye shields are retained on a wearer's head by a resilient band or the like that encircles the wearers head. Although effective for securing the shield in place, such bands are disadvantageous in that they can be uncomfortable for many wearers. The bands are also disadvantageous in that they tend to compress wearer's hairstyles thereby leaving a band-shaped depression in the wearer's hair. Still further, aside from procuring an entirely new shield structure, shields of the prior art do not allow a wearer to vary the lens portion of the shield with regard to its length, thickness, and other characteristics. Many shields of the prior art are disadvantageous for the further reason that they do not allow a wearer to replace all exposed portions of a contaminated shield readily and conveniently.

In light of the foregoing, it becomes clear that there is an appreciable need for an element of eyewear, such as an eye shield, that would provide a solution to one or more of the abovedescribed deficiencies from which prior art devices have suffered. It is still more clear that an eye shield providing a solution to each of the needs left by the prior art while providing a number of heretofore unrealized advantages thereover would represent a marked advance in the art and would in all likelihood perform advantageously relative to eyewear even beyond protective shields.

SUMMARY OF THE INVENTION

Advantageously, the present invention is founded on the broadly stated object of providing an element of eyewear that solves each of the deficiencies that the prior art has been unable to solve while supplying a number of even further advantages thereover.

Stated more particularly, a fundamental object of the invention is to provide an element of eyewear that can provide a wearer with unqualified protection from airborne debris and contaminants. Still more particular objects of the invention include preventing debris and contaminants from reaching portions of a wearer's face, such as the wearer's eyes, nose, and mouth, including from directly in front of the wearer, from beside the wearer, and from above the wearer's eyes.

A related object of the invention is to provide an element of eyewear that can provide an opaque shield for a wearer's eyes from light from above.

Another basic object of the invention is to provide an element of eyewear with a lens or shield portion that can be controlled with regard to its distance from a wearer's face and forehead to accommodate the wearing of eyeglasses, different wearer preferences, and different facial structures.

Still another object of the invention is to provide an element of eyewear that can be securely retained relative to a wearer's head without a need for entirely surrounding the wearer's head with a band or the like.

An even further object of the invention is to provide an element of eyewear that can absorb perspiration from a wearers brow thereby to prevent that perspiration from reaching the wearers eyes and the like.

A further object of the invention is to provide an element of eyewear that enables a wearer to change the length, thickness, angle, tint, and further characteristics of the lens or shield portion of the eyewear without a need for procuring an entirely new element of eyewear.

These and further objects and advantages of the invention will be readily obvious not only to one who has reviewed the present specification and drawings but also to one who has had an opportunity to make use of an embodiment of the present invention for an element of eyewear.

In carrying forth these objects, a most basic embodiment of the present invention for an element of eyewear is founded on a first eyewear portion and a second eyewear portion. At least one projection extends from the first eyewear portion, and at least one aperture is disposed in the second eyewear portion. The first eyewear portion can comprise a lens portion, and the second eyewear portion can comprise a frame portion. Alternatively, the eyewear portions could be disposed oppositely such that the projection would extend from the second eyewear portion, which again could comprise a frame portion, and the aperture could be disposed in the first eyewear portion, which again could comprise a lens portion.

Under even this basic arrangement, the first eyewear portion can be removably and replacably coupled with the second eyewear portion by an insertion of the projection of the first eyewear portion into the aperture in the second eyewear portion. With this, a damaged or contaminated lens portion can be removed from the frame portion and can be replaced by a new or cleaned lens portion without a need for replacing the frame portion. Furthermore, a wearer can replace a lens portion of a given type with a different lens portion of another type or property, such as a different size, material, tint, or other characteristic.

Preferably, the projection from the first eyewear portion will have at least one cross-sectional dimension that is greater than a corresponding cross-sectional dimension of the at least on aperture in the second eyewear portion. For example, the preferred projection will be wider, taller, or wider and taller than the aperture. With this, the projection will be frictionally retained in the at least one aperture. Of course, this could be accomplished in a number of ways. One preferred way is to form the projection partly or entirely from resiliently compressible material, such as resiliently compressible foam or the like. Alternatively, the projection could be mechanically compressible such as by being formed by first and second longitudinally coupled members with a resiliently compressible member, such as a spring, interposed therebetween.

The eyewear certainly could accomplish the foregoing with just a single projection from the first eyewear portion and a single aperture in the second eyewear portion. In such a case, the projection could be an elongate strip of, for example, resiliently compressible foam, and the aperture could be of corresponding size and shape. Alternatively, there could be a plurality of projections and a plurality of apertures corresponding in size, shape, and relative location such that they are disposed to align with the plurality of apertures. With this, the plurality of projections can be received into the plurality of apertures to project therethrough.

In preferred embodiments, the frame portion of the eyewear can have a bridge segment for being disposed adjacent to a forehead of a wearer. In such a case, the plurality of apertures can be disposed in the bridge segment, and the projection or projections can extend from adjacent to an upper edge of the lens portion. Under certain embodiments, the projection or projections can extend from an elongate body portion of resiliently compressible material that is affixed to and extends across an inner surface of the lens portion.

With this, the distal end or ends of the projection or the plurality of projections can pass through the apertures and beyond an inner surface of the bridge segment to contact the forehead of the wearer and to maintain the inner surface of the bridge segment spaced from the forehead of the wearer. Advantageously, the projection or projections and possibly the body portion of resiliently compressible material can cooperate with the bridge segment to prevent debris and other airborne contaminants from reaching a wearers eyes. The body portion of resiliently compressible material and the projection or projections that extend therefrom simultaneously can cooperate to shield the wearer's eyes from light from above. Even further, the resiliently compressible projection or projections can absorb perspiration from the wearer's brow thereby to prevent that perspiration from reaching the wearer's face, particularly his or her eyes.

One can exploit this arrangement to adjust or control the distance between the forehead of the wearer and the lens portion of the eyewear by adjusting or controlling the length of the projection or projections. Alternatively or additionally, the distance between the forehead or brow of the wearer and the lens portion can be controlled by an adjustment of the thickness of the body portion of resiliently compressible material. With this, a wearer desiring to maintain the lens portion more significantly spaced from his or her face to allow, for example, the wearing of eyeglasses under the lens portion can employ projections of increased length or a body portion of increased thickness. The length of the projections and the thickness of the body portion can also be used to accommodate wearers with different physical structures and preference.

In one preferred embodiment, the projections can be formed in multiple sections that are detachably coupled such as along lateral, perforated score lines. Under this arrangement, no, one, or multiple sections can be torn away from the remainder of the projection to alter the length of the projection. By doing so, the wearer will control the amount that the body portion of the projection projects beyond the inner surface of the bridge segment and thus the distance that the lens portion is maintained from his or her face.

It is, of course, important to note that the eyewear could assume a number of forms and could be used for a number of purposes. For example, eyewear according to the present invention could be designed and used for general casual wear. Furthermore, embodiments of the invention could be designed for sports use. Even further still, elements of eyewear embodying the present invention could incorporate shield-type lens portions such that they could be used to great advantage in medical situations to comply with Universal Precaution Guidelines and in painting, spraying, welding, and other situations where ones eyes must be shielded or otherwise protected. In such a case, the lens portion typically would take the form of a panel of transparent material, which could, for example, be flat or arcuate.

Even further advantage can be realized by forming the frame portion of the eyewear with first and second arms with first and second arms fixedly or hingedly coupled to the bridge segment for being disposed to opposite sides of a head of a wearer. Under such a construction, the eyewear can be retained relative to the head of the wearer by contact of the distal end of the projection or projections with the forehead of the wearer and by contact of the arms with the sides of the head of the wearer. With this, the eyewear could be securely retained without a need for any portion thereof resting on the bridge of the wearer's nose and without a need for a band or the like surrounding the wearer's head.

One will appreciate that the foregoing discussion broadly outlines the more important features of the invention to enable a better understanding of the detailed description that follows and to instill a better appreciation of the inventor's contribution to the art. Before an embodiment of the invention is explained in detail, it must be made clear that the following details of construction, descriptions of geometry, and illustrations of inventive concepts are mere examples of the many possible manifestations of the invention.

DETAILED DESCRIPTION OF PREFERRED EMBODIMENTS

As is the case with many inventions, the present invention for an element of eyewear with a detachable lens portion is subject to a wide variety of embodiments. However, to ensure that one skilled in the art will be able to understand and, in appropriate cases, practice the present invention, certain preferred embodiments of the broader invention revealed herein are described below and shown in the accompanying drawing figures.

Figure 1:
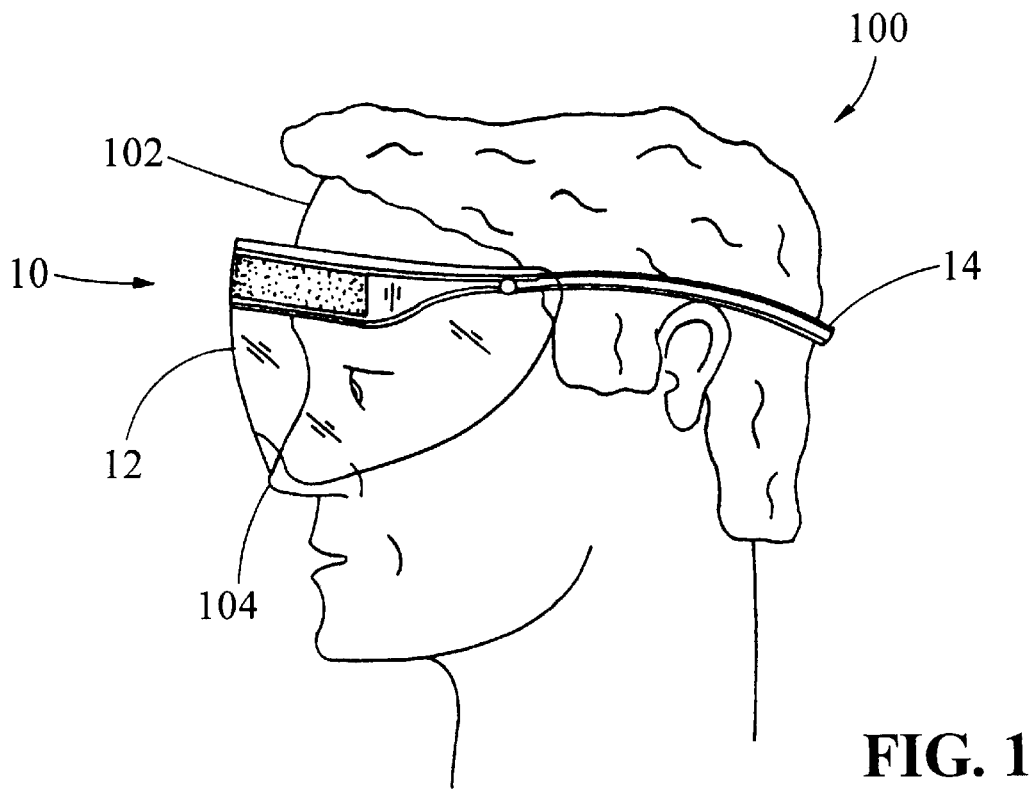
FIG. 1 is a view in side elevation of an embodiment of the present invention for an element of eyewear with a detachable lens portion being worn by a person.

Looking more particularly to the drawings, a preferred embodiment of the present invention for an element of eyewear with a detachable lens portion is indicated generally at 10 in FIG. 1 where the element of eyewear 10 is disposed on a wearer's head 100. There, one sees that the element of eyewear 10 is founded on a lens portion 12 that is removably and replacably coupled to a frame portion 14 as will be discussed more fully hereinbelow. In this embodiment, the lens portion 12 is in the form of a partial shield for protecting a wearer's eyes during, for example, medical procedures, painting tasks, sporting endeavors, and any other circumstance where a shielding of the eyes is necessary or desirable.

Figure 2:
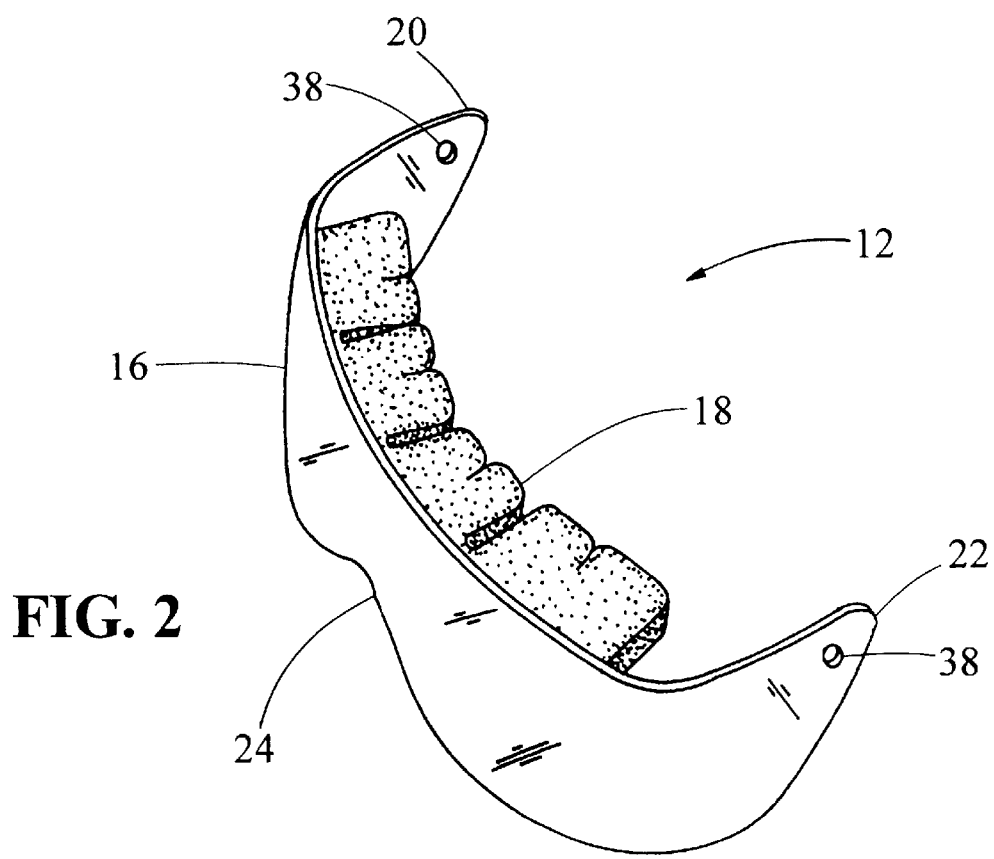
FIG. 2 is a perspective view of a lens portion of the element of eyewear of FIG. 1.

The shield or lens portion 12 is shown apart from the frame portion 14 in FIG. 2. There, one sees that the lens portion 12 is founded on a panel 16 of translucent, typically transparent, material. Of course, one skilled in the art would be well aware of many materials that could be employed to form the panel 16. One presently preferred material is polyester. Where necessary or desirable, the panel 16 could be tinted to shield the wearer's eyes form the sun or other sources of light. Furthermore, the material for the panel 16 could be selected to meet ANSI or other standards for impact or the like. For example, the panel 16 could be formed as a molded polycarbonate shield. In any case, the panel 16 could be formed or machined for aiding in a wearer's vision. More typically, however, the panel 16 will be optically clear such that it will not aid or interfere with the wearer's vision.

As FIG. 1 shows most clearly, the panel 16 is arcuate such that it wraps around a wearer's face from temple to temple. The panel 16 has what may be termed a lower edge that is cut along an arcuate line such that it has a broadest portion below the wearer's eyes and such that it terminates at first and second ends 20 and 22 adjacent to the wearer's temples. One will also note that the panel 16 has an arch portion 24 removed from a central portion thereof for providing clearance for the wearer's nose 104. With this, as will be discussed below, the element of eyewear 10 can be worn by a wearer without a need for contacting the wearer's nose as is commonly required with many types of eyewear according to the prior art.

As one can see from FIG. 2, a plurality of projections 18 extend from an inner surface of the panel 16. Each projection 18 has a proximal end, a distal end, and a body portion. In this exemplary embodiment, there are four projections 18. However, it will be clear that the number of projections 18 is, in many respects, of little consequence to the utility of the present invention. As a result and as will be shown and discussed more fully below, there could be as few as one projection 18 as is shown in the top plan view of FIG. 5 and many more than four projections 18 from the inner surface of the lens portion 12 as is shown in the top plan views of FIGS. 4 and 6. In the embodiment of FIG. 2 where a plurality of projections 18 are provided, each projection 18 can, for example, have a generally rectangular cross section. Each of the projections 18 can taper slightly toward its distal end.

Preferably, the projections 18 will be resiliently compressible. This can be accomplished through material selection, by construction, or both. One skilled in the art will appreciate that, where the projections 18 are resiliently compressible through material selection, the projections 18 could be formed partially or completely from a wide variety of materials. For example, the projections 18 could be formed from natural or synthetic sponge, from rubber, or from any other resiliently compressible material. The projections 18 could be solid, hollow, and/or foamed. The projections 18 can be molded, die cut, formed, or otherwise crafted.

Figure 3:
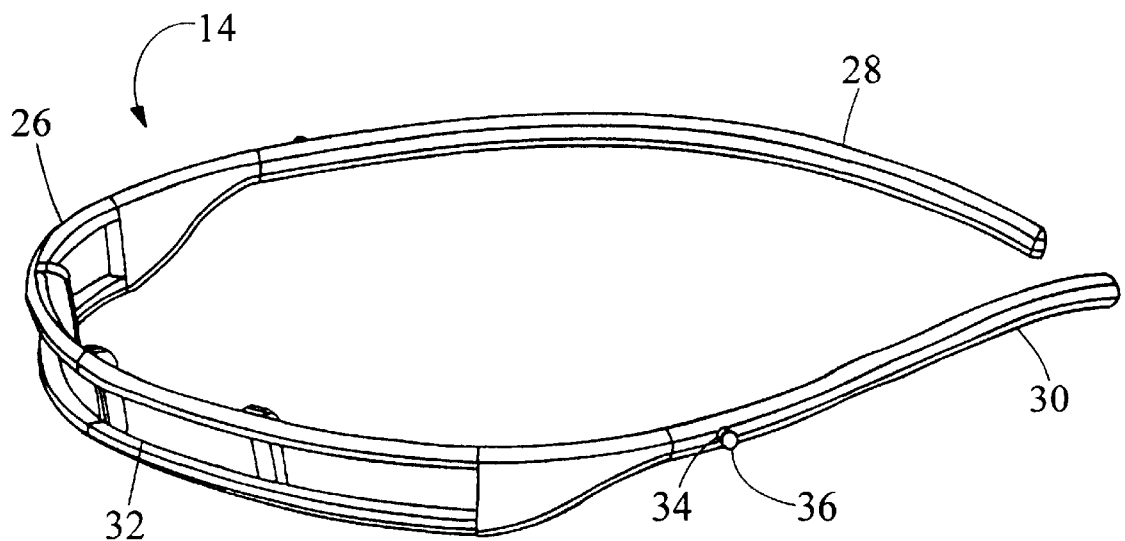
FIG. 3 is a perspective view of a frame portion of the element of eyewear of FIG. 1.

As FIG. 3 shows, the frame portion 14 in this embodiment is formed by a bridge segment 26 that is coupled at a first end to a first leg 28 and at a second end to a second leg 30. The bridge segment 26 could be straight or it could be curved as is shown, for example, in FIGS. 1 and 3. In this embodiment, the first and second legs 28 and 30 are formed integrally with the bridge segment 26 such that they cannot pivot relative thereto. As will be discussed below, however, the first and second legs 28 and 30 could be hingedly coupled to the bridge segment 26 such that the element of eyewear 10 could be folded into a compact configuration. Like the panel and the projections 18, the frame portion 14 could be formed from a wide variety of materials that would readily occur to one skilled in the art. Preferably, the frame portion 14 will provide sufficient rigidity, will be light in weight, and will demonstrate good memory characteristics. One presently preferred material is polycarbonate.

Figure 6:
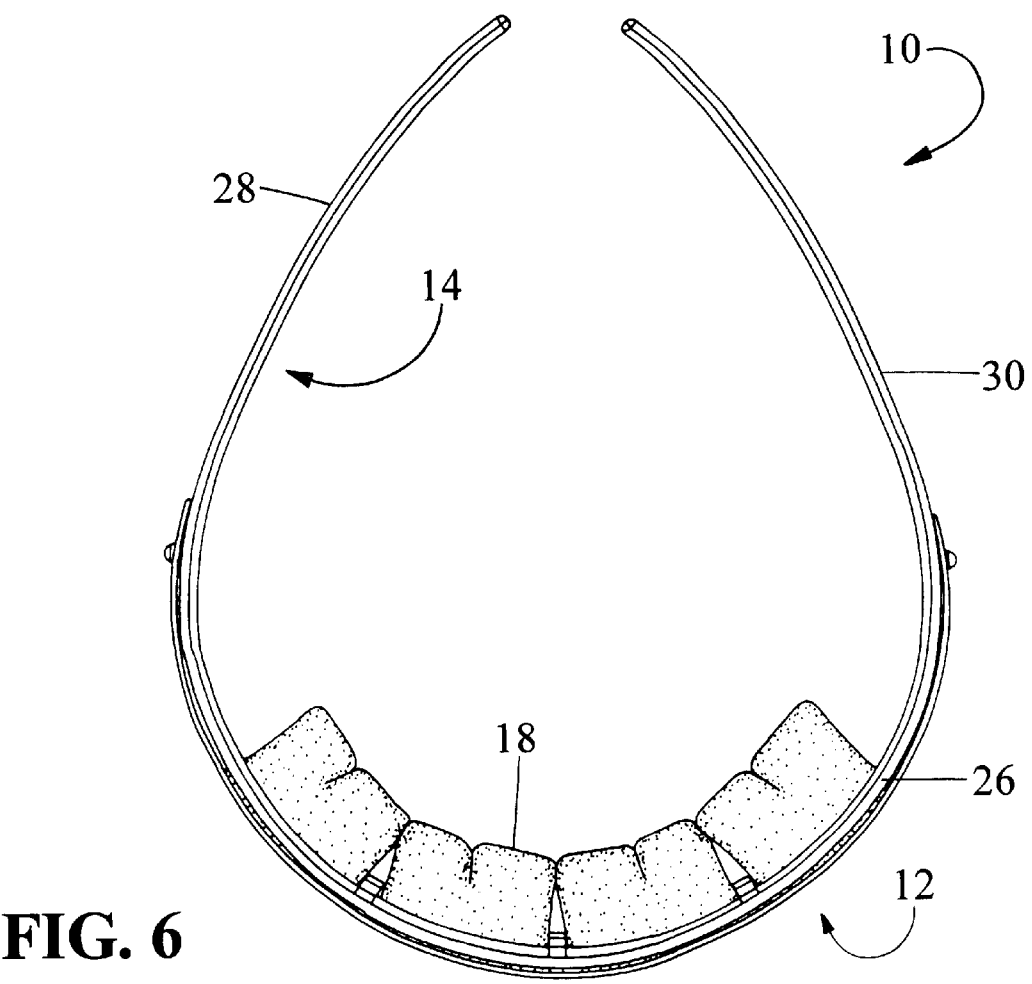
FIG. 6 is a top plan view of the element of eyewear with the lens portion coupled to the frame portion.

A plurality of apertures 32 are disposed in the bridge segment 26. Of course, the plurality of apertures 32 in the bridge portion preferably will correspond in number, location, shape, and orientation to the plurality of projections 18 from the inner surface of the lens portion 12. Each projection 18 can then be received in and pass through its corresponding aperture 32 as is shown in FIG. 6. Advantageously, as FIG. 6 also shows, the projections 18 and the lens and frame portions 12 and 14 in general can be formed such that, when the projections 18 are fully received into and through the apertures 32, the distal portions of the projections 18 will touch or nearly touch. With this, the projections 18 and the bridge segment 26 will cooperate to prevent light, debris, and splattered contaminants from reaching the wearer's eyes from above.

Ideally, each of the plurality of apertures 32 will be slightly smaller in cross section than its corresponding projection 18. With this, by virtue of their resilient compressibility, the projections 18 will tend to be retained frictionally within the apertures 32. As a result, the lens portion 12 will be secured relative to the frame portion 14. As one will also appreciate, however, the lens portion 12 and the frame portion 14 can be readily separated simply by pulling the projections 18 from within the apertures 32.

As one can perceive by combined reference to FIGS. 1 and 6 the distal ends of the projections 18 under this arrangement will contact the wearer's forehead 102. The inner surface of the bridge segment 26 will be maintained spaced away from the wearer's forehead 102 by roughly the distance that the body portions of the plurality of projections 18 project beyond the inner surface of the bridge segment 26.

Advantageously, therefore, a wearer can select from among lens portions 12 with projections 18 having a length designed to accommodate the wearer's preferences or requirements. For example, a wearer who must wear eyeglasses (not shown) can choose a lens portion 12 with relatively long projections 18 such that the bridge portion 26 and thus the panel 16 will be maintained sufficiently distant from the wearer's head that eyeglasses can be worn under the element of eyewear 10. Furthermore, wearer's with different facial characteristics and dimensions can select projections 18 with appropriate lengths to suit their particular requirements.

Figure 7:
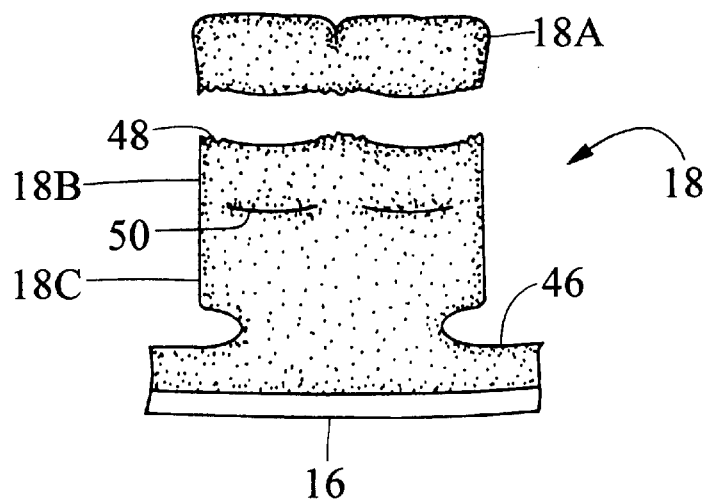
FIG. 7 is a top plan view of an embodiment of a projection from the lens portion.

The embodiment of FIG. 7 shows that the projection 18 or projections 18 can extend from a body portion 46 of resiliently compressible material. Under such a construction, the distance that is maintained between the wearer's face and the panel 16 can be adjusted by controlling the thickness of the body portion 46, which may be done in addition to or as an alternative to adjusting the length of the projection 18 or projections 18. In the embodiment of FIG. 7, the body portion 46 is formed of resiliently compressible material. The body portion 46 is affixed to the inner surface of the panel 16, and the projection or projections 18 extend from the body portion 46.

Although the frictional contact between the projections 18 and the apertures 32 certainly could serve to retain the lens portion 12 in a sufficiently secure manner relative to the frame portion, a secondary coupling means could be employed to ensure that the projections 18 do not inadvertently slide from within the apertures 32. Of course, such a secondary coupling means could take many different forms.

In FIGS. 1–3 and 5, the secondary coupling means comprises short rods 34 with bulbous ends 36 that project from proximal end portions of each of the legs 28 and 30 at the temple area of the frame portion 14 in cooperation with correspondingly sized fastening apertures 38 located adjacent to each of the ends 20 and 22 of the panel 16. With this, the wearer can pop the bulbous ends 36 of the rods 34 through the apertures 38 thereby to fix the lens portion 12 relative to the frame portion 14 still more securely.

Figure 4:
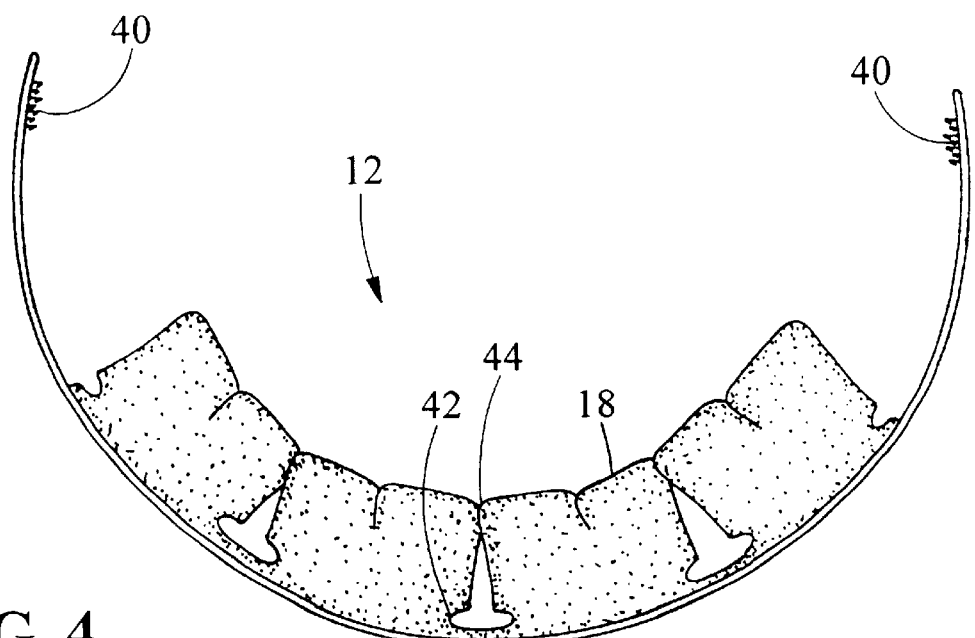
FIG. 4 is a top plan view of an alternative embodiment of the lens portion of the element of eyewear.

An alternative embodiment of the lens portion 12 is shown in FIG. 4. There, the lens portion 12 is again founded on an arcuate panel 16. Also, a plurality of projections 18 again extend from the inner surface of the panel 16 for engaging corresponding apertures 32 in the bridge segment 26 of the frame portion 14. In demonstration of the fact that the number of projections 18 and apertures 32 is of little practical consequence, this embodiment has six projections 18. Of course, an appropriately crafted frame portion 14 (not shown) would have apertures 32 corresponding to the projections 18 in size, shape, location, and number.

Under this preferred construction, the projections 18 are again generally rectangular in cross section. Each of the projections 18 has a narrowed neck portion 42 adjacent to its proximal end and a tapered portion 44 adjacent to its distal end. The tapered portion 44 allows the projections 18 to be pressed through the apertures 32 more easily. The narrowed neck portions 42 can be disposed generally even with the apertures 32 in the bridge segment 26 thereby to provide widened portions of the projections 18 to either side of the bridge segment 26 and to secure the lens portion 12 relative to the frame portion 14 most effectively.

One skilled in the art will appreciate that the secondary coupling means for further fastening the lens portion 12 to the frame portion 14 could take a variety of forms in addition to that shown in FIGS. 1–3 and 5. For example, as FIG. 4 shows, the secondary coupling means could comprise a hook and loop combination with a first component 40, in this case hooks, of the combination disposed adjacent to the first and second ends 20 and 22 of the arcuate panel 16 and a second component of the combination (i.e. loops, which are not shown) disposed adjacent to the proximal ends of the first and second legs 28 and 30 of the frame portion 14. Numerous other secondary coupling means are certainly possible including buttons 52 as shown in FIG. 8, double-sided tape, clips, and still other means.

Figure 5:
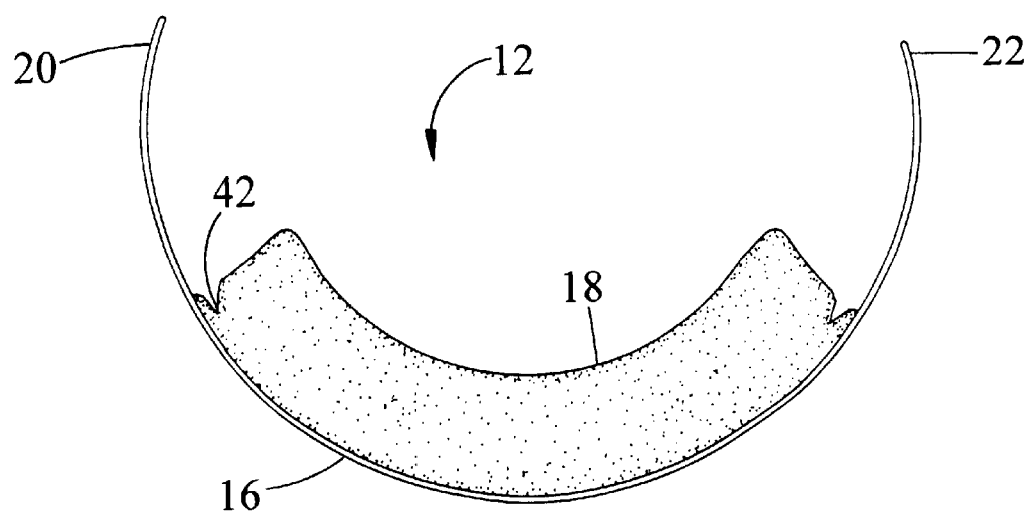
FIG. 5 is a top plan view of another alternative embodiment of the lens portion of the element of eyewear.

Another alternative embodiment of the lens portion 12 is shown in FIG. 5. The lens portion 12 again includes an arcuate panel 16. In this embodiment, however, just one projection 18, which can be formed from resiliently compressible foam, extends from the inner surface of the panel 16. The projection 18 traverses nearly the entire length of the panel 16. The corresponding frame portion 14 of FIG. 9 has a single aperture 32 that traverses substantially the entire bridge segment 26. The projection 18 again has a narrowed neck portion 42 adjacent to its proximal end for better securing the projection 18 within the aperture 32.

Figure 8:
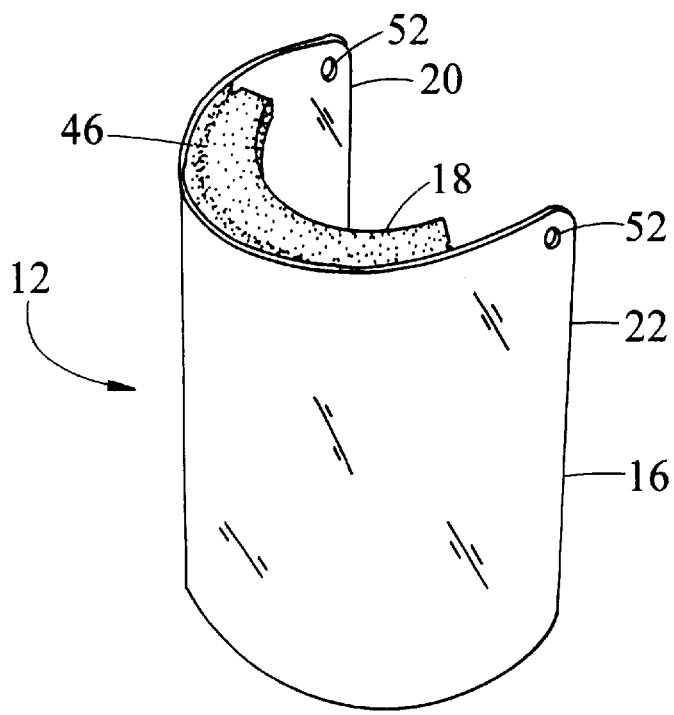
FIG. 8 is a perspective view of an alternative embodiment of the lens portion according to the present invention.
Figure 9:
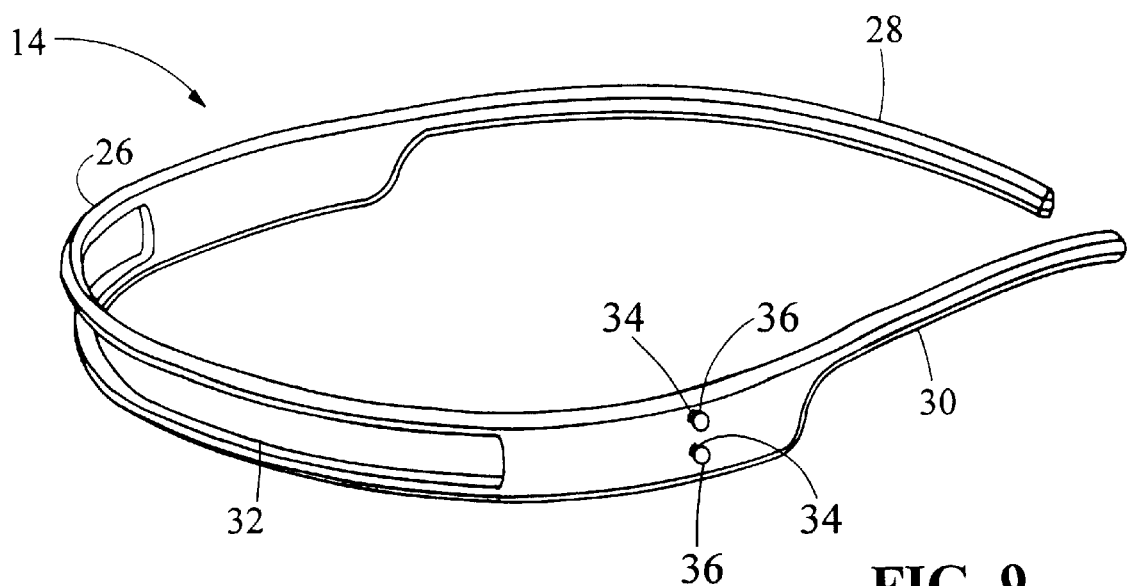
FIG. 9 is a perspective view of an alternative embodiment of the frame portion according to the present invention.

In FIG. 9, upper and lower rods 34 with bulbous end portions 36 project from proximal ends of the first and second legs 28 and 30 of the frame portion 14 for better securing the frame portion 14 to a corresponding lens portion 12 such as that shown in FIGS. 2 and 8. With this, a wearer can choose whether to pop the upper or lower rod 34 and bulbous end 36 into the fastening aperture 38 whereby the wearer can adjust the angle at which the panel 16 is disposed relative to his or her head. Alternatively, although it is not explicitly shown, one will appreciate that the same advantage could be accomplished by providing upper and lower fastening apertures 38. It should also be appreciated that the rod or rods 34 and bulbous end or ends 36 and the fastening aperture or apertures 38 could be oppositely disposed such that the fastening aperture or apertures 38 would be disposed on the frame portion 14 and the rod or rods 34 and the bulbous end or ends 36 would project from the lens portion 12.

As was noted previously, the ability to control the distance between the panel 16 and a wearer's face can be desirable for a number of reasons, including to accommodate eyeglasses and wearer's facial structures. This certainly can be done by choosing from among lens portions 12 with a projection 18 or projections 18 of varying lengths and/or by controlling the thickness of a body portion 46. However, potentially greater advantage can be had by forming each projection 18 so that its length can be adjusted by the wearer. With this, just a single type of projection 18 could be sold or otherwise distributed, and a user can adjust the length of the projection 18 as necessary.

Of course, this could be done in a number of ways. One presently preferred way is depicted in FIG. 7. There, the projection 18 is formed in multiple sections 18A, 18B, and 18C that are detachably coupled along lateral lines 48 and 50. The sections 18A, 18B, and 18C could of course be detachably joined in a number of ways. In this case, the lateral lines 48 and 50 joining the sections 18A, 18B, and 18C are perforated score lines in the resiliently compressible material that forms the projection 18. With this, none, one, or both of sections 18A and 18B can be torn away from the remainder of the projection 18. By doing so, the wearer will control the amount that the body portion of the projection 18 projects beyond the inner surface of the bridge segment 26 and thus the distance that the panel 16 is maintained from his or her face.

One will appreciate that the shape and length of the panel 16 shown, for example, in FIGS. 1 and 2 can be varied widely within the scope of the present invention depending on the needs and goals of the wearer. Although the relatively abbreviated panel 16 certainly could be useful in a number of uses, other applications may require a longer or differently shaped panel for protecting the wearer's eyes, nose, mouth, and face in general. For example, the lens portion 12 shown in FIG. 8, although again arcuate, is based on a generally rectangular panel 16 that would be sufficiently long for having its upper edge disposed above the wearer's eyes and its lower edge disposed somewhat below the wearer's chin thereby providing full facial protection. The embodiment of FIG. 8 also varies in that the secondary coupling means comprises button components 52 disposed adjacent to the first and second ends 20 and 22 of the panel 16. One will further note that the lens portion 12 has a single projection 18 that extends from a body portion 46 of resiliently compressible material.

Figure 10:
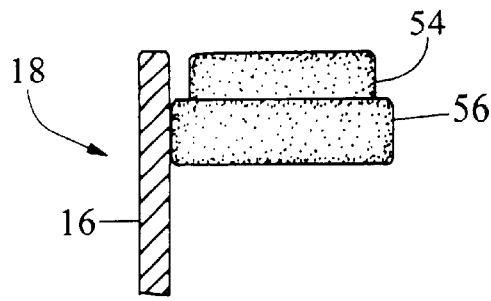
FIG. 10 is a partially sectioned view in side elevation of an alternative embodiment of the projection from the lens portion.

Forming the projections 18 from resiliently compressible material certainly may be preferred. It should be appreciated, however, that other constructions would be well within the scope of the present invention. For example, as FIG. 10 shows, the projection 18 could be made to be resiliently compressible by mechanical means. In this case, the projection 18 is made to be resiliently compressible by a first member 54 that is longitudinally coupled to a second member 56 with one or more resiliently compressible members, such as springs, interposed therebetween.

Figure 11:
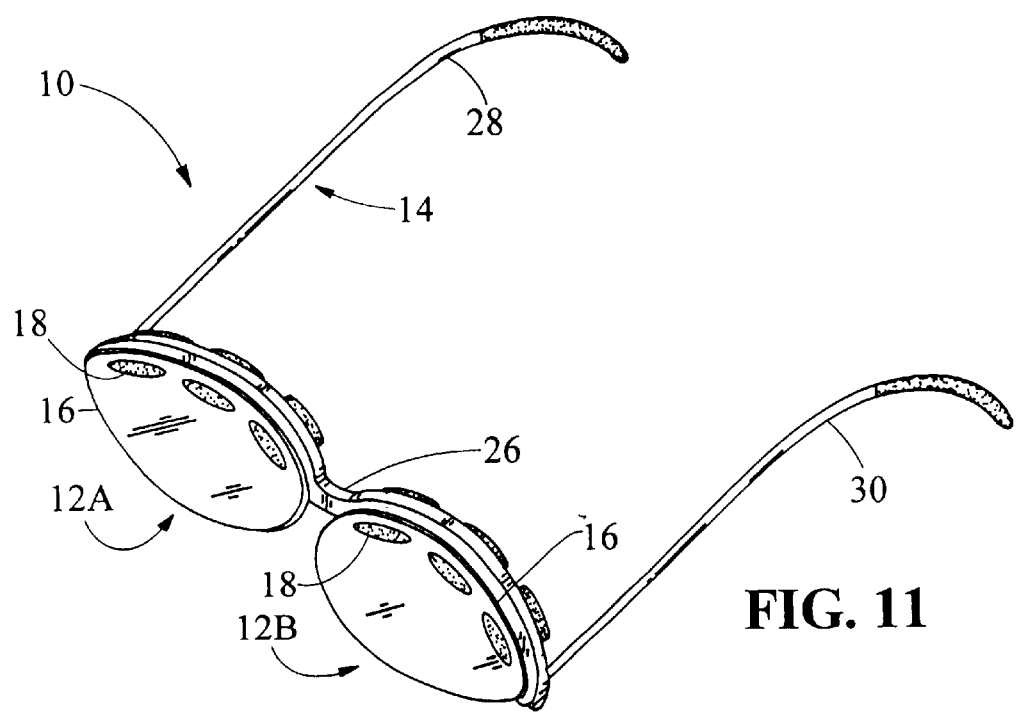
FIG. 11 is a perspective view of another alternative embodiment of the element of eyewear.

The present invention for an element of eyewear 10 has been shown primarily in the form of a shield with a single panel 16 such as would be used for eye protection during medical procedures, painting, and numerous other tasks where eye and face protection against airborne matter is necessary. It must be clear, however, that the element of eyewear 10 could take numerous other forms. For example, the element of eyewear 10 could take the form of a standard pair of eyeglasses or sunglasses as is shown in FIG. 11. There, the element of eyewear 10 incorporates first and second lens portions 12A and 12B that each include a panel 16 of translucent material.

The panels 16 can be tinted and, additionally or alternatively, formed or ground to improve the wearer's eyesight. Each panel 16 has a plurality of projections 18 that extend from adjacent to the upper edge thereof for engaging the bridge segment 26 of the frame portion 14. As is commonly the case with prior art eyeglasses and sunglasses, the first and second legs 28 and 30 in this embodiment are hingedly coupled to the bridge segment 26 so that the element of eyewear 10 can be folded into a compact configuration.

With a plurality of preferred embodiments of the invention disclosed, it will be appreciated by one skilled in the art that numerous changes and additions could be made thereto without deviating from the spirit or scope of the invention. This is particularly true when one bears in mind that the presently preferred embodiments merely exemplify the broader invention revealed herein.

Accordingly, it will be clear that those with major features of the invention in mind could craft embodiments that incorporate those major features while not incorporating all of the features included in the preferred embodiments. Therefore, the following claims are intended to define the scope of protection to be afforded the inventors. Those claims shall be deemed to include equivalent constructions insofar as they do not depart from the spirit and scope of the invention.

It must be further noted that a plurality of the following claims may express certain elements as means for performing a specific function, at times without the recital of structure or material. As the law demands, these claims shall be construed to cover not only the corresponding structure and material expressly described in this specification but also equivalents thereof.

I claim as deserving the protection of Letters Patent:

1. An element of eyewear with a detachable lens portion, the element of eyewear comprising:
   a first eyewear portion;
   a second eyewear portion;
   at least one projection that extends from the first eyewear portion wherein the at least one projection has a proximal end, a distal end, and a body portion with a given length; and
   at least one aperture in the second eyewear portion;
   whereby the first eyewear portion can be removably and replacably coupled with the second eyewear portion by an insertion of the at least one projection of the first eyewear portion into the at least one aperture in the second eyewear portion.

2. The element of eyewear of claim 1 wherein the at least one projection of the first eyewear portion has at least one cross-sectional dimension that is greater than a corresponding cross-sectional dimension of the at least on aperture in the second eyewear portion whereby the at least one projection can be frictionally retained in the at least one aperture.

3. The element of eyewear of claim 2 wherein the at least one projection is resiliently compressible.

4. The element of eyewear of claim 3 wherein at least a portion of the at least one projection is formed from resiliently compressible material.

5. The element of eyewear of claim 4 wherein a plurality of projections are spaced along and extend from a body portion of resiliently compressible material that is affixed to the first eyewear portion, wherein there are a plurality of apertures in the second eyewear portion, and wherein the plurality of projections are disposed to align with the plurality of apertures whereby the plurality of projections can be received into the plurality of apertures to project therethrough.

6. The element of eyewear of claim 5 wherein the first eyewear portion comprises a lens portion and wherein the second eyewear portion comprises a frame portion.

7. The element of eyewear of claim 6 wherein the frame portion has a bridge segment for being disposed adjacent to a forehead of a wearer and wherein the plurality of apertures are disposed in the bridge segment.

8. The element of eyewear of claim 7 wherein each of the plurality of projections has a length greater than a corresponding thickness of the bridge segment of the frame portion whereby the distal ends of each of the plurality of projections can pass beyond an inner surface of the bridge segment to contact the forehead of the wearer.

9. The element of eyewear of claim 1 wherein the first eyewear portion comprises a lens portion and wherein the second eyewear portion comprises a frame portion.

10. The element of eyewear of claim 9 wherein the frame portion has a bridge segment for being disposed adjacent to a forehead of a wearer and wherein the at least one aperture is disposed in the bridge segment.

11. The element of eyewear of claim 10 wherein the element of eyewear comprises an eye shield and wherein the first eyewear portion comprises a panel of translucent lens material.

12. The element of eyewear of claim 11 wherein the at least one projection has a length greater than a thickness of the bridge segment of the frame portion whereby the distal end of the at least one projection can pass beyond an inner surface of the bridge segment to contact the forehead of the wearer.

13. The element of eyewear of claim 12 wherein the frame portion further comprises first and second arms coupled to the bridge segment for being disposed to opposite sides of a head of a wearer whereby the element of eyewear can be retained relative to the head of the wearer by contact of the distal end of the at least one projection with the forehead of the wearer and by contact of the arms with the sides of the head of the wearer.

14. The element of eyewear of claim 13 wherein the at least one projection comprises a member of resiliently compressible material.

15. The element of eyewear of claim 14 wherein the at least one projection extends from an elongate body portion of resiliently compressible material that is affixed to and extends across an inner surface of the eye shield.

16. The element of eyewear of claim 15 wherein there are a plurality of projections that extend from the first eyewear portion, wherein there are a plurality of apertures in the second eyewear portion, and wherein the plurality of projections are disposed to align with the plurality of apertures whereby the plurality of projections can be received into the plurality of apertures to project therethrough.

17. The element of eyewear of claim 1 wherein the body portion of the at least one projection is formed in multiple, detachably coupled sections whereby the length of the body portion can be altered by detaching one or more of the sections of the at least one projection.

18. The element of eyewear of claim 17 wherein the sections of the at least one projection are coupled along lateral lines.

19. The element of eyewear of claim 18 wherein the at least one projection is formed from resiliently compressible material and wherein the lateral lines comprise score lines in the resiliently compressible material.

20. An eye shield with a detachable shield portion, the eye shield comprising:

a shield portion comprising a panel of translucent material with an inner surface and an outer surface;

a frame portion comprising a bridge segment for being disposed adjacent to a forehead of a wearer;

at least one projection that extends from the inner surface of the shield portion wherein the at least one projection has a proximal end, a distal end, and a body portion with a given length; and at least one aperture in the bridge segment of the frame portion;

whereby the first eyewear portion can be removably and replacably coupled with the second eyewear portion by an insertion of the at least one projection of the first eyewear portion into the at least one aperture in the second eyewear portion.

21. The eye shield of claim 20 wherein the at least one projection is resiliently compressible has at least one cross-sectional dimension that is greater than a corresponding cross-sectional dimension of the at least on aperture in the bridge segment of the frame portion whereby the at least one projection can be frictionally retained in the at least one aperture.

22. The eye shield of claim 21 wherein at least a portion of the at least one projection is formed from resiliently compressible material.

23. The eye shield of claim 20 wherein a plurality of projections are spaced along and extend from a body portion of resiliently compressible material that is affixed to the shield portion, wherein there are a plurality of apertures in the bridge segment of the frame portion, and wherein the plurality of projections are disposed to align with the plurality of apertures whereby the plurality of projections can be received into the plurality of apertures to project therethrough.

24. The eye shield of claim 23 wherein the plurality of projections have a length greater than a thickness of the bridge segment of the frame portion whereby the distal ends of the plurality of projections can pass beyond an inner surface of the bridge segment to contact the forehead of the wearer.

25. The eye shield of claim 20 wherein the at least one projection has a length greater than a thickness of the bridge segment of the frame portion whereby the distal end of the at least one projection can pass beyond an inner surface of the bridge segment to contact the forehead of the wearer.

26. The eye shield of claim 25 wherein the frame portion further comprises first and second arms coupled to the bridge segment for being disposed to opposite sides of a head of a wearer whereby the element of eyewear can be retained relative to the head of the wearer by contact of the distal end of the at least one projection with the forehead of the wearer and by contact of the arms with the sides of the head of the wearer.

27. The eye shield of claim 26 wherein the at least one projection comprises a member of resiliently compressible material.

28. The eye shield of claim 27 wherein the at least one projection extends from an elongate body portion of resiliently compressible material that is affixed to and extends across an inner surface of the shield portion.

29. The eye shield of claim 28 wherein there are a plurality of projections that extend from the shield portion, wherein there are a plurality of apertures in the second eyewear portion, and wherein the plurality of projections are disposed to align with the plurality of apertures whereby the plurality of projections can be received into the plurality of apertures to project therethrough.

30. The eye shield of claim 20 wherein the body portion of the at least one projection is formed in multiple, detachably coupled sections whereby the length of the body portion can be altered by detaching one or more of the sections of the at least one projection.

\* \* \* \* \*